United States Patent [19]

Allen et al.

[11] Patent Number: 5,573,908
[45] Date of Patent: Nov. 12, 1996

[54] ADRENERGIC RECEPTOR AS A PROTO-ONCOGENE

[75] Inventors: Lee F. Allen; Robert J. Lefkowitz; Marc G. Caron; Susanna Cotecchia, all of Durham, N.C.

[73] Assignee: Duke University, Durham, N.C.

[21] Appl. No.: 170,684

[22] Filed: Dec. 20, 1993

Related U.S. Application Data

[63] Continuation of Ser. No. 808,322, Dec. 16, 1991, abandoned.

[51] Int. Cl.⁶ ............................. C12Q 1/68; C12N 5/10
[52] U.S. Cl. ............................. 435/6; 435/240.1
[58] Field of Search ........................ 435/7.2, 240.1, 435/6

[56] References Cited

U.S. PATENT DOCUMENTS 4,935,341  6/1990  Bargmann et al. ................. 435/6

OTHER PUBLICATIONS

Schuller, H. M. (1989) Carcinogenesis, vol. 10, No. 9, pp. 1753–1755.
Cotecchia, S. et al. (1988) Proceedings of the National Academy of Sciences, vol. 85, pp. 7159–7163.
D. Julius et al., *Science* 244, 1057–1062 (1989).
D. Young et al., *Cell* 45, 711–719 (1986).
J. Gutkind et al., *Proc. Natl. Acad. Sci. USA* 88, 4703–4707 (1991).
S. Cotecchia et al., *Proc. Natl. Acad. Sci. USA* 87, 2896–2900 (1990).

*Primary Examiner*—Stephanie W. Zitomer
*Assistant Examiner*—Eggerton Campbell
*Attorney, Agent, or Firm*—Bell, Seltzer, Park & Gibson

[57] ABSTRACT

A recombinant cell comprising a host cell containing a recombinant DNA sequence is disclosed. The recombinant DNA sequence comprises vector DNA and DNA which encodes a mammalian adrenergic receptor. The host cell is one capable of undergoing proliferation in response to activation of the adrenergic receptor. In one specific embodiment of the foregoing, the adrenergic receptor includes a mutation in the third cytoplasmic loop thereof which renders the adrenergic receptor constitutively active, and the host cell undergoes proliferation in response to the constitutively active adrenergic receptor. Also disclosed are in vitro assays employing the foregoing which are useful for screening test compounds for antitumor and antiatherogenic activity, along with a diagnostic assay for detecting the oncogenic activation of cells in a patient. The diagnostic assay comprises collecting sample cells which express adrenergic receptors from the patient, and then detecting the presence or absence of a mutation in the adrenergic receptor which renders the receptor constitutively active. The presence of such a mutation indicates the oncogenic activation of the cells.

8 Claims, 7 Drawing Sheets

ADRENERGIC RECEPTOR AS A PROTO-ONCOGENE

This invention was made with Government support under Grant Number NIH-HL 16037 from the National Institutes of Health. The Government may have certain rights to this invention.

This is a continuation of application Ser. No. 07/808,322 filed on Dec. 16, 1991, abandoned.

FIELD OF THE INVENTION

This invention relates to oncogenes in general, and particularly relates to the finding that the $\alpha_{1B}$ adrenergic receptor functions as an oncogene when activated in cells capable of undergoing oncogenic transformation in response thereto.

BACKGROUND OF THE INVENTION

Proto-oncogenes are normal cellular genes whose activated counterparts, the oncogenes, convert cells in which they are expressed from normal cells to tumor cells. Thus, identification of new proto-oncogenes aid in the understanding, diagnosis, and treatment of cancer. See, e.g., C. Bargmann et al., *Detection of Point Mutations in Neu Genes*, U.S. Pat. No. 4,935,341 (1990).

D. Young et al., *Cell* 45, 711–719 (1986), report the identification of a new human oncogene named mas. Unlike other oncogenes, mas is similar to the class of proteins known as G-protein coupled receptors. More recently, G-protein coupled serotonin receptors and G-protein coupled acetylcholine receptors have been shown to induce a neoplastic transformation in fibroblasts transformed therewith. D. Julius et al., *Science* 244, 1057–1062 (1989); J. Gutkind et al., *Proc. Natl. Acad. Sci. USA* 88, 4703–4707 (1991). We have previously shown that mutations can be introduced into the $\alpha_1$-adrenergic receptor to render it constitutively active, S. Cotecchia et al., *Proc. Natl. Acad. Sci. USA* 87, 2896–2900 (1990), but it has heretofore been unknown whether adrenergic receptors might also function as proto-oncogenes. The present invention is based upon our ongoing investigations in this area.

SUMMARY OF THE INVENTION

A first aspect of the present invention is a recombinant cell comprising a host cell containing a recombinant DNA sequence. The recombinant DNA sequence comprises vector DNA and DNA which encodes a mammalian adrenergic receptor, with the adrenergic receptor being expressed in the host cell. The host cell is one capable of undergoing proliferation in response to activation of the adrenergic receptor.

In one specific embodiment of the foregoing, the adrenergic receptor includes a mutation in the third cytoplasmic loop thereof rendering the receptor constitutively active, and the host cell undergoes proliferation in response to the constitutively active adrenergic receptor.

A second aspect of the present invention is an in vitro assay procedure. the procedure comprises contacting a test compound to a recombinant cell as given above, and then detecting whether or not the test compound inhibits proliferation of the cell. The assay is useful for screening test compounds for antitumor and antiatherogenic activity.

A third aspect of the present invention is a diagnostic assay for detecting the oncogenic activation of cells in a patient. The assay comprises collecting sample cells which express adrenergic receptors from the patient, and then detecting the presence or absence of a mutation in the adrenergic receptor which renders the receptor constitutively active. The presence of such a mutation indicates the oncogenic activation of the cells, and may therefore further serve both as a prognostic marker and a screening test to identify a subpopulation of patients which may be amenable to specific treatment modalities.

The foregoing and other objects and aspects of the present invention are explained in the drawings provided herein and the specification set forth below.

DETAILED DESCRIPTION OF THE INVENTION

Figure 1A:
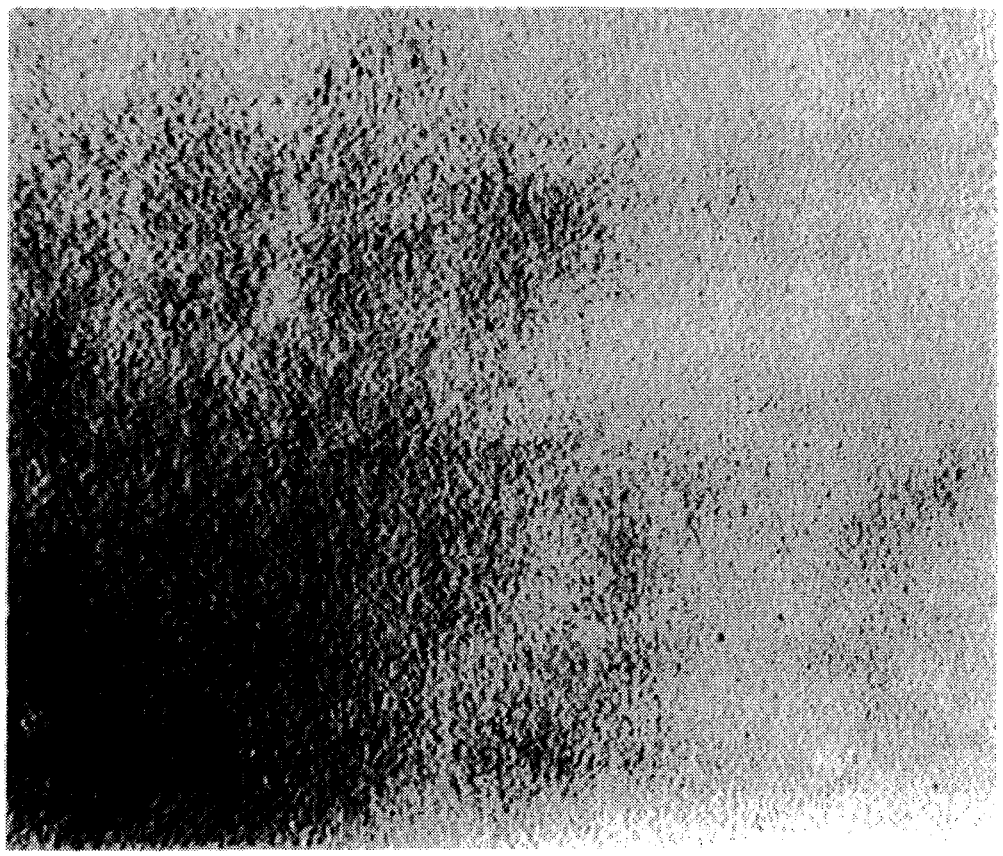
FIG. 1. Agonist-dependent transformation of RAT-1 fibroblasts transfected with $\alpha_{1B}$-ADR c-DNA. RAT-1 fibroblasts were transfected with the retroviral expression vector, pZIP-NeoSV(X) 1, containing the $\alpha_{1B}$-ADR c-DNA. Cells were then cultured for 4 weeks in medium containing 5% fetal bovine serum (FBS) in the absence (A) or presence of 10 μM norepinephrine (B). No foci were observed in the absence of added ligand (A). A single focus of transformation is shown in agonist-treated cultures (B).

The production of cloned genes, recombinant DNA, vectors, transformed host cells, proteins and protein fragments by genetic engineering is well known. See, e.g., U.S. Pat. No. 4,761,371 to Bell et al. at Col. 6 line 3 to Col. 9 line 65; U.S. Pat. No. 4,877,729 to Clark et al. at Col. 4 line 38 to Col. 7 line 6; U.S. Pat. No. 4,912,038 to Schilling at Col. 3 line 26 to Col. 14 line 12; and U.S. Pat. No. 4,879,224 to Wallner at Col. 6 line 8 to Col. 8 line 59. The disclosures of all U.S. Patent references cited herein are to be incorporated herein by reference.

A vector is a replicable DNA construct. Vectors comprise plasmids, viruses (e.g., adenovirus, cytomegalovirus, retroviruses), phage, and integratable DNA fragments (i.e., fragments integratable into the host genome by recombination). The vector replicates and functions independently of the host genome, or may, in some instances, integrate into the host genome itself. Vectors are used herein to express adrenergic receptors in host cells. An expression vector is a replicable DNA construct in which a gene encoding an adrenergic receptor is operably linked to suitable control sequences capable of effecting the expression of the adrenergic receptor in a suitable host. The need for such control sequences will vary depending upon the host selected and the transformation method chosen. Generally, control sequences include a transcriptional promoter, an optional operator sequence to control transcription, a sequence encoding suitable mRNA ribosomal binding sites, and sequences which control the termination of transcription and translation. An origin of replication may be provided either by construction of the vector to include an exogenous origin, such as may be derived from SV 40 or other viral (e.g. Polyoma, Adenovirus, VSV, or BPV) source, or may be provided by the host cell chromosomal replication mechanism. If the vector is integrated into the host cell chromosome, the latter is often sufficient.

DNA regions are operably linked or operably associated when they are functionally related to each other. For example, a promoter is operably linked to a coding sequence if it controls the transcription of the sequence; or a ribosome binding site is operably linked to a coding sequence if it is positioned so as to permit translation.

Transformed host cells are cells which have been transformed or transfected with vectors containing a gene encoding an adrenergic receptor using recombinant DNA techniques. Transformed host cells employed in carrying out the present invention express the adrenergic receptor, as noted above.

Cloned genes encoding adrenergic receptors used in the present invention can be of any species of origin, including mouse, rat, rabbit, cat, hamster, porcine, and human, but are preferably of mammalian origin. Any type of adrenergic receptor can be employed, including $\alpha_1$ adrenergic receptors (e.g., $\alpha_{1A}$, $\alpha_{1B}$, and $\alpha_{1C}$ adrenergic receptors), $\alpha_2$ adrenergic receptors (e.g., $\alpha_{2A}$, $\alpha_{2B}$, and $\alpha_{2C}$ adrenergic receptors), and $\beta$ adrenergic receptors (e.g., $\beta_1$, $\beta_2$, and $\beta_3$ adrenergic receptors). The $\alpha_1$ and $\beta$ adrenergic receptors are preferred, and the $\alpha_1$ receptors are most preferred. The term "adrenergic receptor" as used herein is intended to encompass natural allelic variations in the receptor genes, and is intended to encompass the gene in both its proto-oncogene and oncogene form unless specified otherwise. As noted above, one group of genes employed in the present invention are those encoding an adrenergic receptor containing a mutation in the third cytoplasmic loop thereof (and particularly in the carboxyl terminus of the third cytoplasmic loop) which would render the receptor constitutively active so that the host cell in which the gene is expressed undergoes proliferation in response to the constitutively active receptor. Examples of constitutively activated adrenergic receptor mutants include, but are not limited to, hamster $\alpha_{1B}$-ADR mutant c-DNAs which produce (i) three substitutions at positions 288, 290 and 293 in the carboxyl terminus of the third intracellular loop ($Arg^{288} \Delta Lys$, $Lys^{290} \rightarrow His$, and $Ala^{293} \rightarrow Leu$), or (ii) substitutions at either or both of positions 290 and 293 in the carboxyl terminus of the third intracellular loop ($Lys^{290} \rightarrow His$, and $Ala^{293} \rightarrow Leu$), as described in S. Cotecchia et al., Proc. Natl. Acad. Sci. USA 87, 2896–2900 (1990); and the corresponding homologs thereof in other mammalian species and other adrenergic receptors.

Host cells employed in carrying out the present invention are cells capable of undergoing proliferation (e.g., oncogenic transformation) in response to the activation of the receptor. Typically the host cell is a nonterminally differentiated cell such as a fibroblast cell (e.g., NIH 3T3 fibroblast cells and RAT-1 fibroblast cells). The cells may be grown in in vitro culture, such as a monolayer.

In vitro assay procedures of the present invention are, as noted above, useful for the identification of potential antitumor and antiatherogenic drugs. With the cells described above, the procedure may be carried out a variety of ways. For example, an adrenergic receptor agonist such as norepinephrine can be contacted to the recombinant cell in an amount effective to activate proliferation of the cell, and the detecting step carried out by detecting whether the test compound inhibits the proliferation of the cell caused by the adrenergic receptor agonist. Alternatively, the adrenergic receptor can include a mutation in the third cytoplasmic loop thereof rendering the receptor constitutively active, as noted above, so that the host cell undergoes proliferation in response thereto, and the detecting step carried out by detecting whether the test compound inhibits the activation of proliferation of the cell caused by the constitutively active adrenergic receptor.

Diagnostic assays of the present invention are useful, as noted above, for detecting the oncogenic activation of cells in a patient. This may be carried out to identify new oncogenic mutations, to confirm the type of tumor in a particular patient, or to prescreen patients for a predisposition to develop cancer in the future. In addition, they may serve as both a prognostic marker and a screening test to identify a subpopulation of patients which may be amenable to specific treatment modalities. Patients to be tested are typically human, but veterinary applications, such as with dogs and cats, are also contemplated.

The diagnostic method comprises collecting sample cells which express adrenergic receptors from the patient and then detecting the presence or absence of a mutation in the adrenergic receptor which renders the receptor constitutively active. The presence of the mutation indicates the oncogenic activation of the cells. Cells may be tumor cells, or may be white blood cells when the assay is carried out as a pre-screening procedure. The detecting step may be carried out by any suitable means, such as polymerase chain reaction (PCR) or ligase chain reaction (LCR). Preferably, the detecting step is directed to detecting mutations in the third cytoplasmic loop (particularly the carboxyl terminus thereof) which render the receptor constitutively active. Pairs of probes which will serve as PCR primers for the adrenergic receptor, or a portion thereof such as the third cytoplasmic loop, may be used in accordance with the process described in U.S. Pat. Nos. 4,683,202 and 4,683,195. The LCR, which also employs pairs of probes, is also known. See, e.g., How LCR Works, Science 254, 1292 (29 Nov. 1991).

The present invention is explained in greater detail in the following nonlimiting Examples. As used herein "mm" means millimeters, "g" means grams, "mg" means milligrams, "µg" means micrograms, "ml" means milliliters, "M" means Molar, "µM" means microMolar "nM" means nanoMolar, "pM" means picoMolar, "µCi" means microCuries, "GBq" means GigaBequerels, and temperatures are given in degrees Centigrade unless otherwise indicated.

EXAMPLE 1

$\alpha_{1B}$-ADR expression results in agonist-dependent focus formation.

To investigate the functional consequences of $\alpha_{1B}$-ADR expression on cell growth, the $\alpha_{1B}$-ADR c-DNA was cloned into a defective retroviral vector, pZIP-NeoSV(X) 1 (C. Cepko, Cell 37, 1053 (1984)) and then transfected into RAT-1 fibroblasts.

Transfection was carried out as follows: RAT-1 fibroblasts were seeded at a density of $2\times10^5$ cells in Dulbecco's modified Eagle's medium (DMEM) (Gibco) containing 5% fetal bovine serum (FBS) in 100 mm dishes. Cells were grown overnight, then transfected with 10 μg of DNA (expression vector alone [pZIP-NeoSV(X)1] or containing the $\alpha_{1B}$-ADR, $\alpha_{1B}$-ADR mutant [discussed in Example 3 below] or activated Ha-ras c-DNAs) by calcium phosphate precipitation (B. Cullen, *Methods Enzymol.* 152, 684 (1987)). The $\alpha_{1B}$-ADR used herein was the hamster $\alpha_{1B}$-ADR described in S. Cotecchia et al., *Proc. Natl. Acad. Sci. USA* 85, 7159–7163 (1988). After 16 hours, the DNA precipitate was removed, the cells washed and grown for 24 hours in complete medium. Cells were split 1:5, allowed to attach overnight and then cultured in DMEM with 5% FBS alone, supplemented with 10 μM norepinephrine (NE) or G418 (300 μg/ml). Dishes were supplemented with NE daily, and fed every 3 days with fresh medium.

Figure 1B:
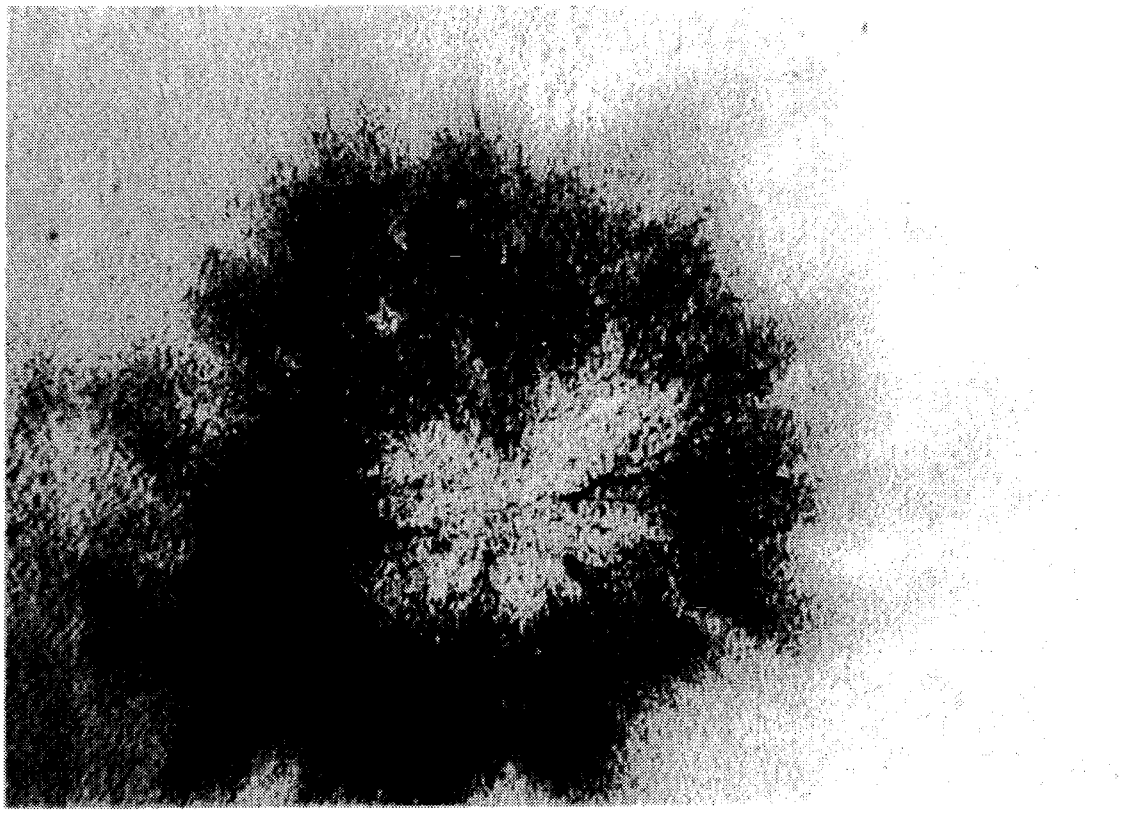

After transfection of plasmid DNA into RAT-1 fibroblasts, no change in phenotype or focal cell overgrowth was observed after 4 weeks in culture in the absence of added agonist (FIG. 1A). The cells formed a uniform monolayer in culture, and became arrested upon growing to confluence through contact inhibition. However, agonist stimulation (NE) reproducibly resulted in the induction of the transformed phenotype with the generation of focus formation in confluent monolayers within two to three weeks (FIG. 1B). Within foci, cells manifest the malignant phenotype with the loss of normal density-dependent growth inhibition, resulting in increased cellular packing. Cells also demonstrated increased refractility and exhibited a disordered cellular orientation. Focus formation was strictly agonist-dependent, and also was not observed in untransfected fibroblasts or those transfected with expression vector alone. The initial frequency of agonist-induced focus formation in RAT-1 fibroblasts was low when compared with focus formation resulting from transfection with the activated ras oncogene (Table 1). Agonist-induced foci represented approximately 15–25% of transfected clones with the number of G418 resistant colonies (40–60/dish) assessed in duplicate transfections. Parallel experiments employing NIH 3T3 fibroblasts resulted in a marked increase in the frequency of agonist-induced focus formation (Table 1) with no significant change in the transfection efficiency. These cells, however, also exhibited a high background of spontaneous transformation in control and untreated cells.

TABLE 1

RAT-1 or NIH 3T3 fibroblasts transfected with expression vector alone or containing the $\alpha_{1b}$ADR, $\alpha_{1B}$ADR mutant or ras c-DNAs.[1]

|  | RAT-1 Foci No. | | NIH 3T3 Foci No. | |
| --- | --- | --- | --- | --- |
| DNA | −NE | +NE | −NE | +NE |
| Vector | 0 | 0 | 10 | 12 |
| α1-B | 0 | 8 | 12 | 85 |
| α1-B, mutant | 0 | 11 | nd | nd |
| RAS | 206 | 197 | 160 | 180 |

[1]Cells were cultured for 3 weeks in the presence or absence of 10 μM norepinephrine (NE), supplemented daily, in medium containing 5% FBS. The number of transformed foci were scored after 4 weeks of culture. Results represent the average duplicate determinations from two independent experiments which agreed within 25%; nd = not determined.

The ability of catecholamines to induce transformation of fibroblasts transfected with the $\alpha_{1B}$-ADR suggests a role for the $\alpha_{1B}$-ADR in regulating mitogenesis, and identifies its gene as a proto-oncogene. While oncogenes, the activated form of proto-oncogenes, are capable of inducing transformation with high efficiency, their precursors are less competent or may even be incompetent. Thus, the number of foci initially generated by constant agonist stimulation may be a reflection of the relatively low intrinsic activity of the unactivated receptor proto-oncogene.

EXAMPLE 2

Maintenance of the transformed phenotype requires continuous receptor activation.

The dependency of focus formation on transfection with $\alpha_{1B}$-ADR c-DNA and continuous activation of this receptor by catecholamines, implicates the $\alpha_{1B}$-ADR c-DNA in activating transmembrane signaling pathways which result in cellular transformation. Whether continued agonist-induced receptor activation is required for the maintenance of this transformed phenotype was next investigated. Multiple cell lines established from individual foci of transformed RAT-1 fibroblasts showed no spontaneous focus formation when maintained in culture in the absence of added agonist (Table 2). On reexposure to agonist, however, these cells showed a markedly enhanced ability for focus generation compared with the initially transfected population, inducing transformed foci at significantly increased rates within two to three weeks (Table 2). Focus formation, however, remained strictly agonist-dependent and could be inhibited by concurrent administration of the selective $\alpha_1$-antagonist, prazosin (data not shown). The absence of focus formation in unstimulated focus-derived cells provides evidence for the essential role of receptor activation in maintenance of the transformed phenotype.

Figure 2A:
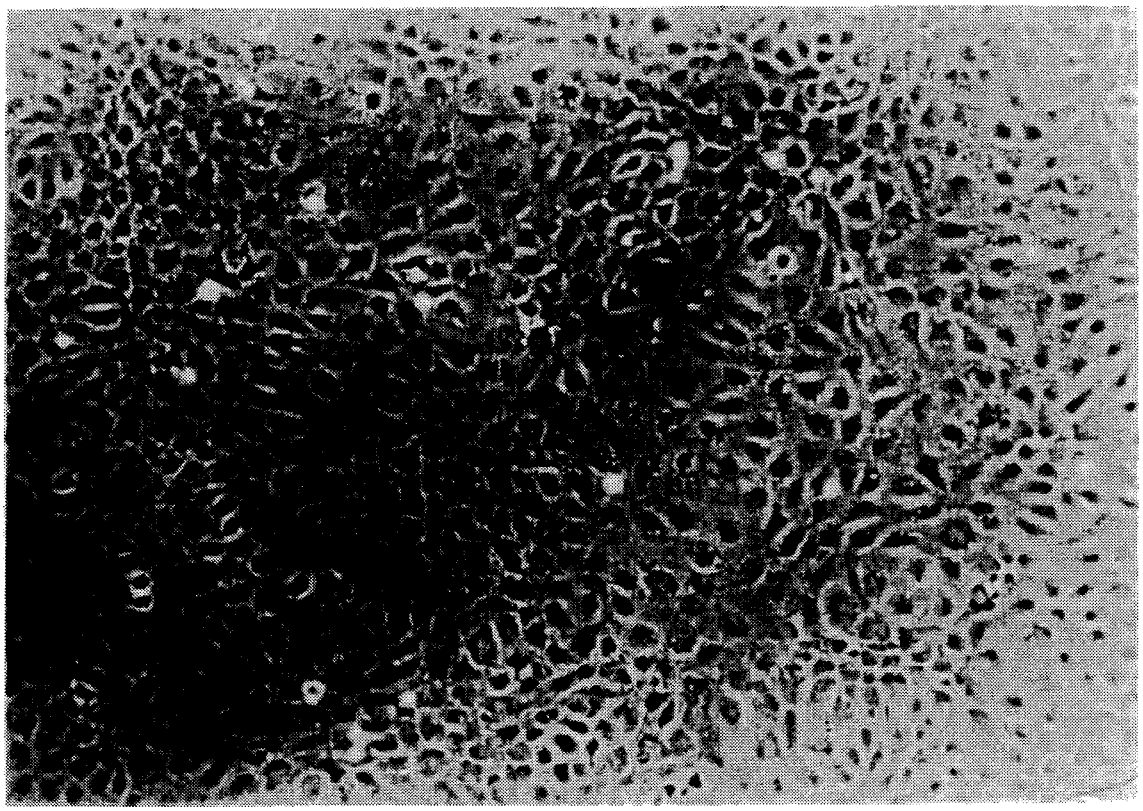
FIG. 2. Agonist-dependent transformation of RAT-1 fibroblasts transfected with the $\alpha_{1B}$-ADR c-DNA. The morphology of a representative RAT-1 fibroblast cell line derived from a single transformed focus expressing the $\alpha_{1B}$-ADR is shown. Cells were plated at a density of 5×10$^5$ cells per 100 mm dish in DMEM containing 5% FBS, and grown in the absence of added ligand (A), in the presence of 10 μM norepinephrine (NE) (B) or 10 μM NE and 1 μM prazosin (C) for 36 hours. Cells exhibited the normal phenotype when cultured in the absence of NE (A), but reverted to the transformed phenotype in the presence of agonist (B). Concurrent antagonist treatment (C) blocked agonist-induced transformation.
Figure 2B:
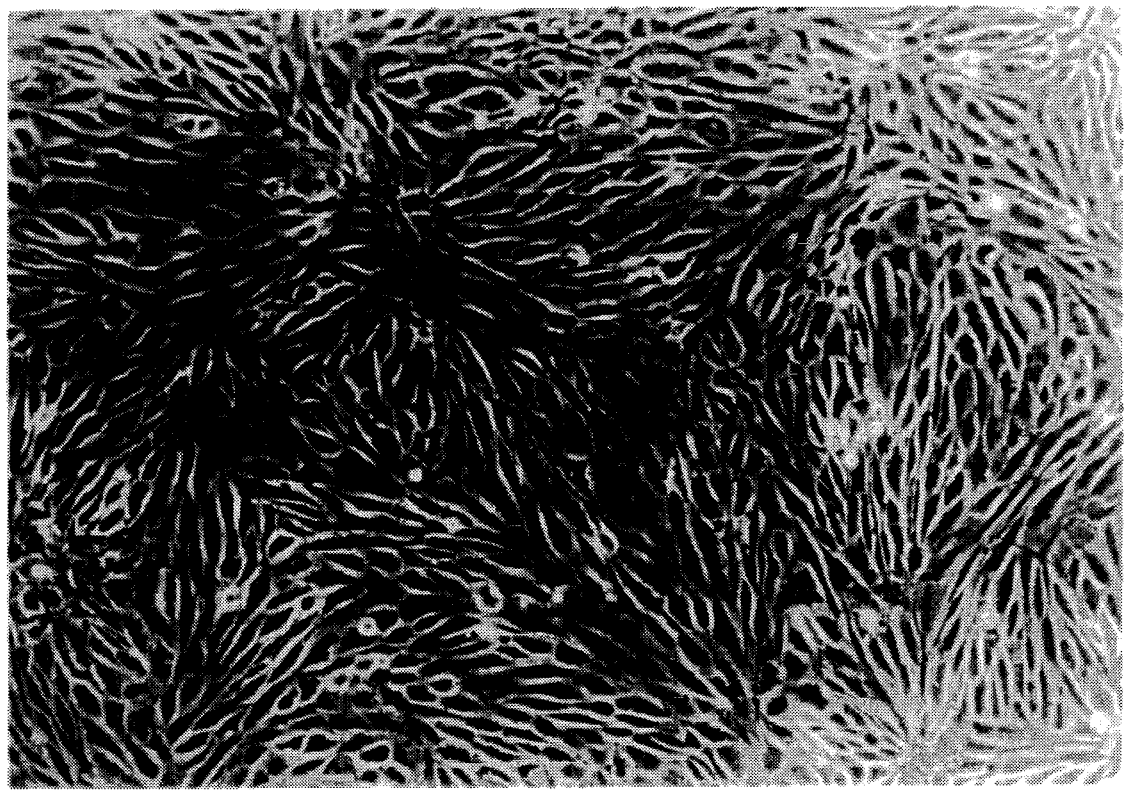
Figure 2C:
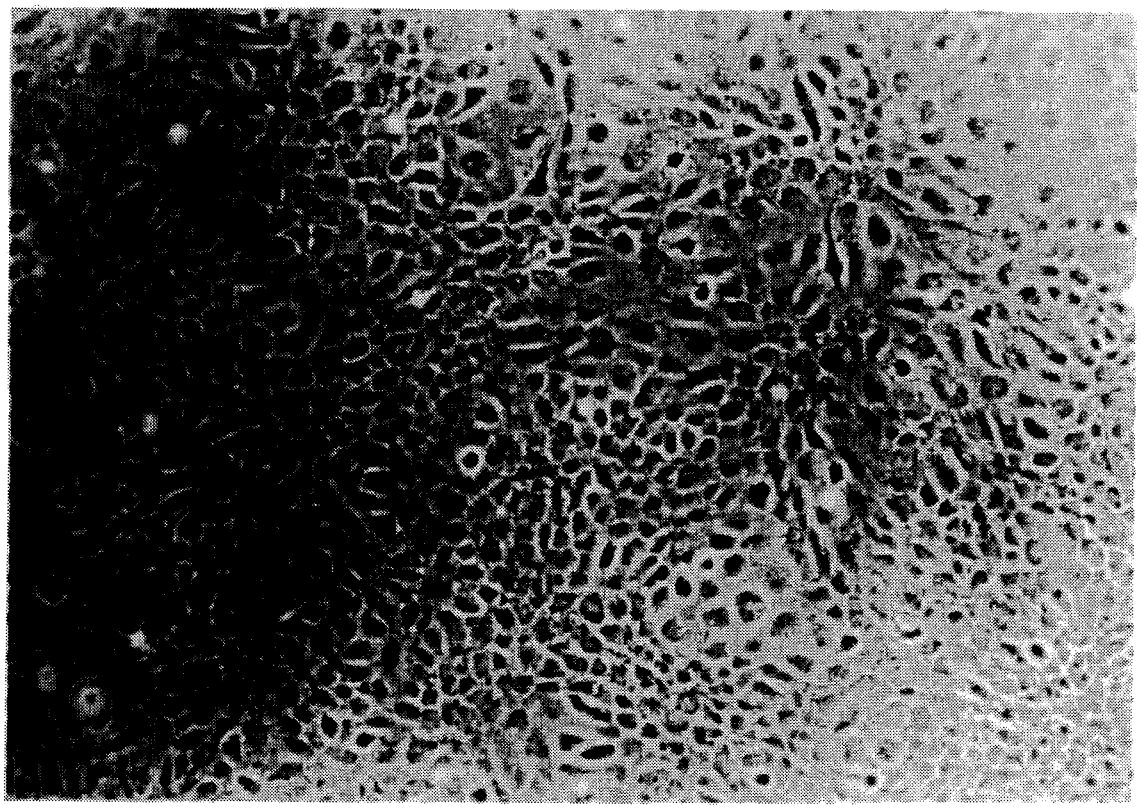

Morphologically, cells expressing the $\alpha_{1B}$-ADR exhibited the normal phenotype, when cultured in the absence of catecholamines (FIG. 2A). In contrast, the same cells, when grown in the presence of NE, demonstrated an agonist-dependent alteration in cellular morphology with a loss in cellular orientation and decreased adhesiveness (FIG. 2B). They appeared transformed with spindle shaped, non parallel sheets of cells forming multilayered aggregates. This disordered pattern of growth was blocked by concurrent incubation of the cells with prazosin, which reverted the cells to the untransformed phenotype (FIG. 2C). These results confirm the conditional nature of transformation of RAT-1 fibroblasts by the $\alpha_{1B}$-ADR, a process requiring continuous agonist-induced receptor activation.

TABLE 2

Focus formation in focus derived RAT-1 fibroblasts.[1]

|  | RAT-1 Foci No. | |
| --- | --- | --- |
| DNA | −NE | +NE |
| Vector | 0 | 0 |
|  | 0 | 0 |
| α1-B | 0 | 75 |
|  | 0 | 80 |
| α1-B, mutant | 45 | >500, sheets |
|  | 65 | >500, sheets |
| PAS | >500 | >500 |
|  | 450 | 460 |

[1]Cell lines were established from cells transfected with the expression vector (pZIP-NeoSV(X)1) alone or from separate transformed foci of RAT-1 fibroblasts transfected with vector containing the $\alpha_{1B}$ADR, $\alpha_{1b}$ADR mutant or ras c-DNAs; two clones are shown for each. Cells were plated in 100 mm dishes at a density of $5 \times 10^5$ cells per dish, and cultured in medium containing 5% FBS in the presence or absence of 10 μM norepinephrine (NE). After 3 weeks of growth, the number of foci was scored. Results represent the means of duplicate determinations from two independent experiments which agreed within 20%.

EXAMPLE 3

Mutational alteration of the $\alpha_{1B}$-ADR results in proto-oncogene activation.

Having established that the $\alpha_{1B}$-ADR could function as a proto-oncogene, we could now investigate whether mutational alteration of this receptor, which induces constitutive activity, would result in proto-oncogene activation and enhance the oncogenic potential of the $\alpha_{1B}$-ADR. To test this hypothesis, an $\alpha_{1B}$-ADR mutant c-DNA producing three substitutions at positions 288, 290 and 293 in the carboxyl terminus of the third intracellular loop (Arg$^{288}\rightarrow$Lys, Lys$^{290}\rightarrow$His, and Ala$^{293}\rightarrow$Leu) as described in S. Cotecchia et al., *Proc. Natl. Acad. Sci. USA* 87, 2896–2900 (1990), was subcloned into the pZIP-NeoSV(X) 1 retroviral vector and transfected into RAT-1 fibroblasts as described in Example 1 above. Expression of this mutant receptor resulted in malignant transformation with focus formation in vitro at initial rates comparable to cells expressing the wild type receptor (Table 1). Restimulation of focus-derived cell lines with agonist, however, resulted in an enhanced ability for focus generation with a quantitative increase in focus number (Table 2), the $\alpha_{1B}$-ADR mutant transfected cells attained rates of focus formation comparable to that of the activated ras oncogene. In addition, the latency period to focus formation was decreased in these cell lines with foci appearing within 7 days compared with 14 to 21 days in cells transfected with the wild type receptor. Further, while focus formation was markedly augmented by agonist administration, it was not absolutely agonist-dependent with the generation of foci in unstimulated cells (Table 2). Morphologically, these cells formed broad sheet-like plaques of transformed cells, rather than the discrete focal cell overgrowths seen in cells expressing the wild type $\alpha_{1B}$-ADR (data not shown). These cell lines appear constitutively activated, exhibiting the malignant phenotype independent of agonist supplementation. In addition, NE-induced focus formation is significantly augmented, reaching the levels observed with the known oncogene, ras. Because of this enhanced transformed phenotype of the $\alpha_{1B}$-ADR mutant transfected cell lines, this mutant receptor was termed the "oncomutant". Conservative mutational alteration of the $\alpha_{1B}$-ADR, thus, appears to activate the transforming activity of this proto-oncogene, enhancing its oncogenic potential.

EXAMPLE 4

The $\alpha_{1B}$-ADR is overexpressed and activates transmembrane signaling pathways in transformed foci.

Cell lines established from foci of transformed RAT-1 fibroblasts exhibited high levels of $\alpha_{1B}$-ADR expression as assessed by the binding of the $\alpha_{1B}$-ADR antagonist, 2{b-(4-hydroxy-3-[$^{125}$I]iodophenyl) ethylaminomethyl}-tetralone ([$^{125}$I]-HEAT; BE-225). Receptor concentrations were in the range of 3 to 5 pmoles/mg of protein in different clones (Table 3), representing an approximately 10 fold higher level of receptor expression, when compared with the level in tissues normally expressing this receptor. The Kd of [$^{125}$I] HEAT and Ki of NE were in agreement with values established for this receptor (S. Cotecchia et al., *Proc. Natl. Acad. Sci. USA* 85, 7159 (1988)). Cell lines derived from foci arising after transfection with the $\alpha_{1B}$-ADR mutant demonstrated receptor expression at levels of 2 pmoles/mg of protein (Table 3), and exhibited the enhanced agonist affinity previously reported (S. Cotecchia et al., supra). Untransfected RAT-1 fibroblasts or cells transfected with vector alone, on the other hand, showed no specific binding.

Therefore, cells giving rise to transformed foci overexpress the $\alpha_{1B}$-ADR, establishing a role for this receptor in mediating the process of neoplastic transformation.

Since RAT-1 fibroblasts do not normally express the $\alpha_{1B}$-ADR, their ability to mediate functional coupling of this receptor to polyphosphoinositide (PI) hydrolysis was investigated. In focus-derived fibroblasts, like cells which normally express the $\alpha_{1B}$-ADR, receptor activation resulted in phospholipase C (PLC) mediated PI hydrolysis with a 400 to 800% increase in total inositol phosphates following NE stimulation (Table 3). In cell lines expressing the $\alpha_{1B}$-ADR mutant, NE induced a 900 to 1000% increase in inositol phosphates (Table 3); this level of PI hydrolysis was only seen in cells expressing the wild type receptor with a two fold higher level of receptor expression. In contrast, no coupling was observed in cells transfected with vector alone or in wild type RAT-1 fibroblasts, which lack the receptor. The $\alpha_{1B}$-ADR, appearing on the surface of RAT-1 fibroblasts following transfection, therefore, functionally couples to PI hydrolysis in these cells. Whether receptor coupling to PLC actually mediates the $\alpha_{1B}$-ADR's ability to induce malignant transformation in these cells, however, remains speculative. Coupling of this receptor to alternate G proteins or effector systems may be responsible for triggering uncontrolled cell proliferation.

TABLE 3

Parameters of ligand binding and activation of PI hydrolysis in RAT-1 fibroblast cell lines expressing the $\alpha_{1B}$ADR or $\alpha_{1B}$ADR mutant.

| Receptor | Ligand Binding | | | NE Stimulated PI Hydrolysis |
|---|---|---|---|---|
| | NE Ki (nM) | [$^{125}$I] HEAT Kd (pM) | [$^{125}$I] HEAT Bmax (pmol/mg) | Rmax (% increase) |
| Vector | — | — | 0 | 0 |
| | — | — | 0 | 0 |
| α1-B | 5,815 | 44.1 | 5.1 | 758 |
| | 5,333 | 38.3 | 2.7 | 410 |
| α1-B, mutant | 42 | 37.9 | 2.2 | 861 |
| | 47 | 46.3 | 2.6 | 954 |

In Table 3, RAT-1 fibroblast cell lines transfected with expression vector alone or derived from transformed foci ($\alpha_{1B}$ADR or $\alpha_{1B}$ADR mutant) were selected with G418 (300 μg/ml). Ligand binding was performed on membranes prepared from two clones of each in accordance with known techniques (S. Cotecchia et al., *Life Sci.* 37, 2389 (1986)). For saturation binding analysis, [$^{125}$I] HEAT concentrations ranged from 10 to 500 pM, nonspecific binding was determined using 1 μM prazosin; in competition experiments, the radioligand concentration was 100 pM. Ligand binding parameters were determined using computerized iterative nonlinear regression analysis (P. Munson, *Methods in Enzymol.* 92, 5432 (1983)). For assessment of receptor coupling to PI hydrolysis, cells were plated in 30 mm dishes, and labeled overnight with 3 μCi/ml of myo-[2-$^3$H(N)]-inositol (1Ci=37 GBq; NEN Research Products) in DMEM containing 3.3% FBS in accordance with known techniques (S. Cotecchia et al., *Proc. Natl. Acad. Sci. USA* 87, 2896 (1990)). After 40 minute stimulation of cells with 10 μM norepinephrine (NE), inositol phosphates were extracted, and separated on AG 1-X8 anion exchange columns (Bio-Rad Labs) in accordance with known techniques (S. Cotecchia et al., *Proc. Natl. Acad. Sci. USA* 87, 2896 (1990)). Total inositol phosphates were eluted with 1M ammonium formate/0.1M formic acid. R$_{max}$ indicates the percentage increase of total labeled inositol phosphates over basal levels following NE stimulation. Results represent the mean of triplicate determinations of two to three independent experiments, which agreed within 20%.

EXAMPLE 5

"Oncomutant" expressing cell lines exhibit a markedly enhanced rate of mitogenesis.

Figure 3A:
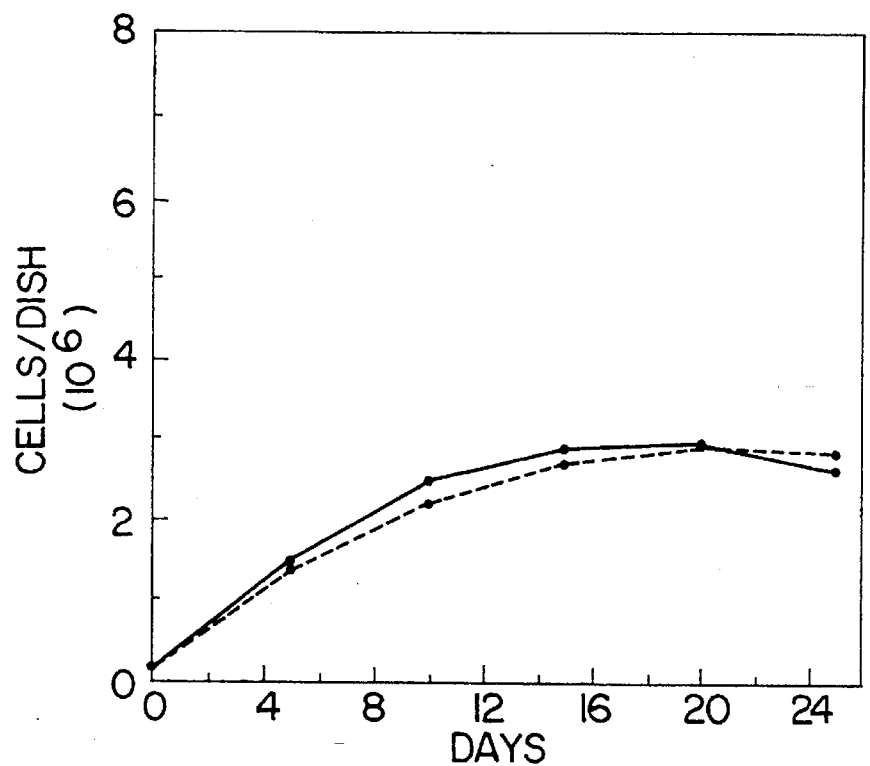
FIG. 3. Growth curves of G418 selected RAT-1 fibroblast cell lines transfected with vector alone (A), or expressing the $\alpha_{1B}$-ADR (B) or $\alpha_{1B}$-ADR mutant (C) in the absence (——) or presence (---) of norepinephrine (NE). Cells were plated in 100mm dishes at a density of 5×10$^5$ cells per dish in DMEM containing 5% FBS. After 24 hours, half the dishes received daily supplementation with 10 μM NE, and all dishes were fed with fresh medium every 2–3 days. At each time point, cells were trypsinized and cell counts determined using an electronic particle counter (Coulter Electronics). Values represent the mean of duplicate determinations of a representative experiment, which agree within 6%.
Figure 3B:
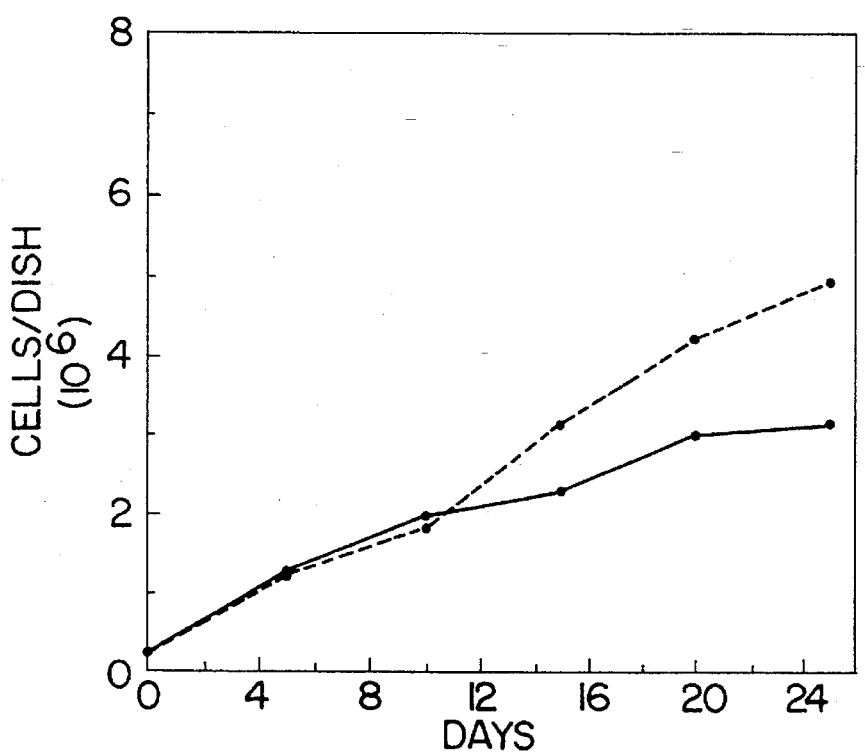

Focus formation represents a morphologic manifestation of agonist-induced transformation, and implies the loss of contact inhibition, a normal growth regulatory process. To quantitate receptor-mediated effects on mitogenesis, basal and NE-stimulated growth rates were assessed on cell lines expressing the wild type or mutant $\alpha_{1B}$-ADRs. Control, vector transfected, cells showed no significant difference in the rate of cell proliferation in the presence or absence of catecholamines (FIG. 3A). In the absence of NE, $\alpha_{1B}$-ADR expressing cells grew at nearly control levels, reaching the same saturation density as control cells by day 25. The addition of catecholamines to these cells, however, resulted in an augmented rate of cell proliferation, surpassing control levels by day 12, and reached a final cell density (day 25) that was 1.9 times control levels (FIG. 3B). Thus, catecholamines appear to be competent mitogens in these cells acting through the $\alpha_{1B}$-ADR. The ability of NE alone to induce an 11 fold increase in DNA synthetic activity in serum free medium, provides additional evidence for a direct mitogenic effect of catecholamines; an effect which could be blocked by prazosin, but not by $\alpha_2$ (idazoxan or yohimbine) or $\beta$ (propranolol) adrenergic receptor; antagonists (data not shown).

Figure 3C:
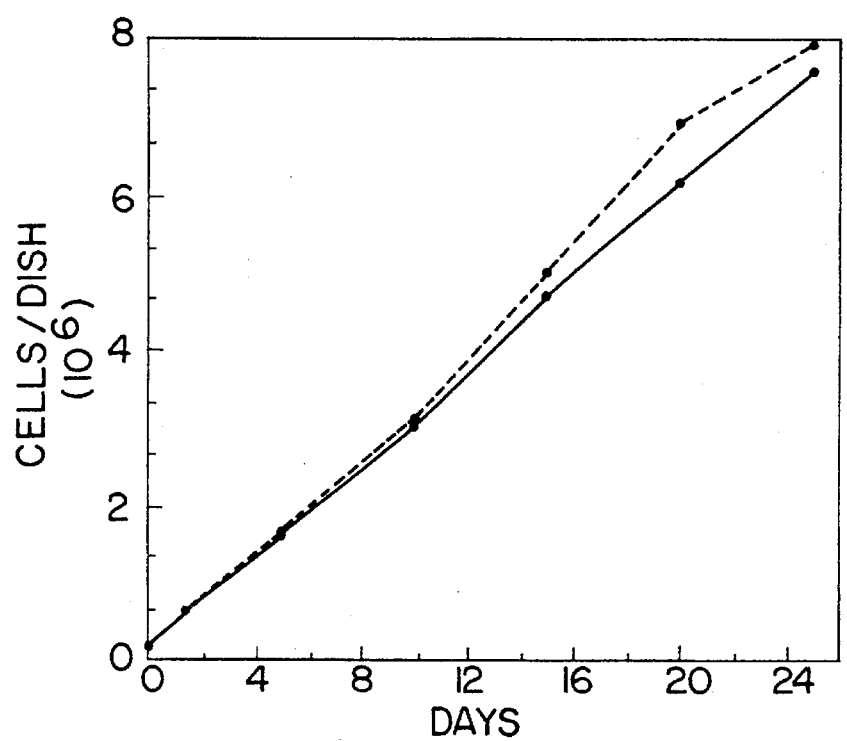

"Oncomutant" expressing cell lines demonstrated a more pronounced mitogenic response than was observed in agonist-stimulated cells expressing the wild type $\alpha_{1B}$-ADR (FIG. 3C). They exhibited a significantly shortened doubling time with cell counts surpassing control levels earlier (day 8), and a 3 fold increase in final cell density compared with control cells. In addition, proliferative activity in these cell lines was maximally activated even in the absence of catecholamine supplementation. Proto-oncogene activation, therefore, results not only in the loss of contact inhibition, but also enhances the rate of mitogenesis in focus-derived cell lines. The faster doubling time and greater saturation densities of cell lines expressing the $\alpha_{1B}$-ADR mutant suggests that these cells exhibit a more highly malignant phenotype. Mutational alteration of the $\alpha_{1B}$-ADR, through amino acid substitution in the third cytoplasmic loop, thus appears to result in the activation of this G-protein-coupled receptor proto-oncogene. "Oncomutant" expressing cell lines demonstrate a more aggressive transformed phenotype, and appear constitutively active with focus formation and maximal growth rates independent of agonist administration.

EXAMPLE 6

Transformed foci possess tumorigenic potential in nude mice.

In vitro assays of transformation, such as the focus formation assay, do not always translate into tumorigenic potential in vivo. In vivo tumorigenesis assays employing nude mice provide a more sensitive assay of true oncogenic potential (O. Fasano et al., *Mol. Cell. Biol.* 4, 1695 (1984)). To assess tumor forming ability, focus-derived cell lines were injected into CD1 nude mice.

Injection of nude mice was carried out as follows: RAT-1 fibroblasts and G418 selected fibroblast cell lines derived from transformed foci or from cells transfected with vector alone were cultured in DMEM containing 5% FBS for 14 days in the presence of 10 µM norepinephrine (NE). Cells were trypsinized, washed and resuspended in serum free DMEM, and $5 \times 10^6$ cells injected at two sites in 21–28 day old female nu/nu CD1 mice (Charles River Labs). Animals were monitored at two day intervals for the development of tumors over a 4 to 8 week period. For ligand binding studies, the animals were sacrificed and tumor tissue rapidly excised and frozen in liquid nitrogen. Membranes were prepared by resuspending tissue fragments in 50 mM Tris buffer (pH 7.4) containing 150 mM NaCl, 50 mM EDTA, 0.1 µg trypsin inhibitor, 0.1 µg leupeptin and 2 mg bacitracin, and homogenizing them with a Polytron at maximum speed. The particulate fraction was collected by centrifugation at 19,000 g for 10 min. The pellet was then washed once in the same buffer, Dounce homogenized, filtered through cheesecloth and the membranes used for ligand binding as described in TABLE 3.

Subcutaneous inoculation of 4 lines expressing the $\alpha_{1B}$-ADR reproducibly resulted in tumorigenesis with the generation of fibrosarcomas in greater than 90% of tested animals (11/12) within a 3 week period. Four cell lines expressing the $\alpha_{1B}$-ADR mutant also induced tumors when injected (16/16), and further demonstrated an enhanced ability for tumorigenesis with a decreased period of latency (2 weeks versus 3 weeks) and increased tumor size compared with lines expressing the wild type receptor. No tumors were observed with injection of RAT-1 fibroblasts or fibroblasts transfected with vector alone after 8 weeks. Examination of the tumor tissue as described above revealed $\alpha_{1B}$-ADR expression with receptor concentrations in the range of 05 to 6 pmoles/mg of protein. Activation of the $\alpha_{1B}$-ADR, therefore, is able to induce a cascade of biochemical and physiological events, which result in the transformation of RAT-1 fibroblasts to cells that are tumorigenic in vivo. Mutational activation of this proto-oncogene augments its oncogenic potential, resulting in a marked enhancement of cell growth and tumorigenesis.

The foregoing examples directly demonstrate the potential of the $\alpha_{1B}$-ADR to activate signal transduction pathways that can abrogate normal growth control mechanisms. The prominent functional role of the $\alpha_{1B}$-ADR in several body systems, e.g. hepatic regeneration and vascular smooth muscle proliferation indicate a role for this G-protein coupled receptor proto-oncogene in hepatic tumorigenesis and atherogenesis. These examples are illustrative of the present invention, and are not to be construed as limiting thereof. The invention is defined by the following claims, with equivalents of the claims to be included therein.

That which is claimed is:

1. An in vitro assay procedure, comprising:

contacting a test compound to a recombinant cell, the recombinant cell comprising a mammalian host cell containing a heterologous DNA molecule, the heterologous DNA molecule comprising vector DNA and DNA which encodes a mammalian $\alpha_1$-adrenergic receptor, wherein said mammalian $\alpha_1$-adrenergic receptor is expressed in said host cell, and wherein said recombinant cell undergoes proliferation in response to activation of said mammalian $\alpha_1$-adrenergic receptor; and detecting whether or not said test compound inhibits the proliferation of said recombinant cell.

2. An assay method according to claim 1, further comprising the step of contacting an adrenergic receptor agonist to said recombinant cell in an amount effective to activate proliferation of said recombinant cell, and wherein said detecting step is carried out by detecting whether said test compound inhibits the proliferation of said recombinant cell caused by said adrenergic receptor agonist.

3. An assay method according to claim 1, wherein said mammalian $\alpha_1$-adrenergic receptor includes a mutation in the third cytoplasmic loop thereof rendering said receptor constitutively active, wherein said recombinant cell undergoes proliferation in response to said constitutively active adrenergic receptor, and wherein said detecting step is carried out by detecting whether said test compound inhibits the proliferation of said recombinant cell caused by said constitutively active mammalian $\alpha_1$-adrenergic receptor.

4. A method according to claim 1, wherein said host cell is a fibroblast cell.

5. A method according to claim 1, wherein said recombinant cell is grown as a monolayer in in vitro culture.

6. An assay method according to claim 1, wherein said mammalian $\alpha_1$-adrenergic receptor includes a mutation in the third cytoplasmic loop thereof rendering said receptor constitutively active, wherein said recombinant cell undergoes proliferation in response to said constitutively active adrenergic receptor, and wherein said detecting step is carried out by detecting whether said test compound inhibits the proliferation of said recombinant cell caused by said constitutively active mammalian $\alpha_1$-adrenergic receptor.

7. An in vitro assay procedure, comprising:

contacting a test compound to a recombinant cell grown as a monolayer in in vitro culture, the recombinant cell comprising a mammalian fibroblast host cell containing a heterologous DNA molecule, the heterologous DNA molecule comprising vector DNA and DNA which encodes a mammalian $\alpha_1$-adrenergic receptor, wherein said mammalian $\alpha_1$-adrenergic receptor is expressed in said host cell, and wherein said recombinant cell undergoes proliferation in response to activation of said mammalian $\alpha_1$-adrenergic receptor; and detecting whether or not said test compound inhibits the proliferation of said recombinant cell.

8. An assay method according to claim 7, further comprising the step of contacting an adrenergic receptor agonist to said recombinant cell in an amount effective to activate proliferation of said recombinant cell, and wherein said detecting step is carried out by detecting whether said test compound inhibits the proliferation of said recombinant cell caused by said adrenergic receptor agonist.

* * * * *

UNITED STATES PATENT AND TRADEMARK OFFICE
CERTIFICATE OF CORRECTION

PATENT NO. : 5,573,908

DATED : November 12, 1996

INVENTOR(S) : Allen et al.

It is certified that error appears in the above-indentified patent and that said Letters Patent is hereby corrected as shown below:

Col. 1, line 59, replace "procedure. the" with --procedure. The--.

Col. 3, line 56, replace "Δ Lys," with --→ Lys,--.

Signed and Sealed this

Third Day of June, 1997

Attest:

BRUCE LEHMAN

Attesting Officer     Commissioner of Patents and Trademarks